United States Patent
Onodera et al.

(10) Patent No.: US 12,023,197 B2
(45) Date of Patent: Jul. 2, 2024

(54) ULTRASONIC DIAGNOSTIC APPARATUS

(71) Applicant: CANON MEDICAL SYSTEMS CORPORATION, Otawara (JP)

(72) Inventors: Hideo Onodera, Nasushiobara (JP); Shingo Toyoda, Utsunomiya (JP); Shinichiro Kikuchi, Otawara (JP); Shuta Fujiwara, Nasushiobara (JP); Yuji Kuwana, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 154 days.

(21) Appl. No.: 17/402,028

(22) Filed: Aug. 13, 2021

(65) Prior Publication Data

US 2022/0054107 A1 Feb. 24, 2022

(30) Foreign Application Priority Data

Aug. 18, 2020 (JP) .................................. 2020-138261

(51) Int. Cl.
*A61B 8/00* (2006.01)
*F16M 11/24* (2006.01)

(52) U.S. Cl.
CPC .............. *A61B 8/4405* (2013.01); *A61B 8/44* (2013.01); *F16M 11/24* (2013.01); *A61B 8/4218* (2013.01); *A61B 8/461* (2013.01); *A61B 8/462* (2013.01); *F16M 2200/021* (2013.01)

(58) Field of Classification Search
CPC ......... A61B 8/4218; A61B 8/44; A61B 8/461; A61B 2560/0437; A61B 8/4405; A61B 8/462; A61B 4/462; F16M 11/24; F16M 2200/021; F16M 2200/08

See application file for complete search history.

(56) References Cited

U.S. PATENT DOCUMENTS

2018/0028160 A1* 2/2018 Cho ......................... A61B 8/44
2018/0368806 A1* 12/2018 Toyoda .................... A61B 8/54

FOREIGN PATENT DOCUMENTS

| | | | | |
|---|---|---|---|---|
| CN | 209548000 U | | 10/2019 | |
| CN | 112097018 A | * | 12/2020 | ............... A61B 8/44 |
| EP | 3536244 A1 | * | 9/2019 | ........... A61B 8/4209 |
| JP | 04-108433 A | | 4/1992 | |
| JP | 2002-017452 A | | 1/2002 | |
| JP | 2008295920 A | * | 12/2008 | |
| JP | 2010-068858 A | | 4/2010 | |
| JP | 2015-39601 A | | 3/2015 | |

OTHER PUBLICATIONS

Japanese Office Action issued Mar. 12, 2024, in Japanese Application No. 2020-138261, citing documents 15-18, therein, 3 pages.

* cited by examiner

*Primary Examiner* — Tan Le
(74) *Attorney, Agent, or Firm* — Oblon, McClelland, Maier & Neustadt, L.L.P.

(57) ABSTRACT

In one embodiment, an ultrasonic diagnostic apparatus includes: a main body configured to generate an ultrasonic image; a body housing configured to house the main body; a display/operation panel configured to operate the main body and display the ultrasonic image; and a lifter on which the display/operation panel is placed, the lifter being attached to the body housing and configured to adjust height of the display/operation panel from a floor in each of an electric mode and a manual mode.

9 Claims, 12 Drawing Sheets

ULTRASONIC DIAGNOSTIC APPARATUS

CROSS-REFERENCE TO RELATED APPLICATION

This application is based upon and claims the benefit of priority from Japanese Patent Application No. 2020-138261, filed on Aug. 18, 2020, the entire contents of which are incorporated herein by reference.

FIELD

Disclosed embodiments relate generally to an ultrasonic diagnostic apparatus.

BACKGROUND

An ultrasonic diagnostic apparatus transmits an ultrasonic pulse or an ultrasonic continuous wave, which is generated by transducers included in an ultrasonic probe, into an object's body. Then, the ultrasonic diagnostic apparatus converts reflected ultrasonic signals, which are caused by difference in acoustic impedance between respective tissues inside the object, into electric signals so as to non-invasively acquire information inside the object. A medical examination using an ultrasonic diagnostic apparatus can readily generate and acquire medical images such as tomographic images and/or three-dimensional images inside an object by bringing the ultrasonic probe into contact with the body surface, and thus, is widely applied to morphological diagnosis and functional diagnosis of an organ.

In general, the ultrasonic diagnostic apparatus includes a display for displaying the generated medical images and an operation panel for operating the ultrasonic diagnostic apparatus. The display is configured to include for example, a display panel. The operation panel includes various switches, a trackball, a touch panel, for example. In the following description, the display and the operation panel may be collectively referred to as a display/operation panel.

Many ultrasonic diagnostic apparatuses are configured to allow the height of the display/operation panel to be adjusted. A user, such as a doctor or an ultrasonic examination technologist, can adjust the height of the display/operation panel to a position where the medical image can be easily observed or the user can easily operate the ultrasonic diagnostic apparatus, depending on the posture of the user when examining the object and/or the height and sitting height of the user.

The height of the display/operation panel is adjusted by a lifter on which the display/operation panel is placed or installed. Some conventional ultrasonic diagnostic apparatuses have a manual type lifter that allows the user to manually adjust the height, and some conventional ultrasonic diagnostic apparatuses have an electric type lifter that adjusts the height by driving a motor.

The manual type lifter imposes a greater operational burden on the user than the electric type lifter.

On the other hand, the electric type lifter may become inconvenient when the height of the display/operation panel cannot be adjusted because of possible power supply failure to the lifter, or possible failure of the electric function around the motor of the lifter even when the main body of the ultrasonic diagnostic apparatus does operate with the power.

DETAILED DESCRIPTION

In one embodiment, an ultrasonic diagnostic apparatus includes: a main body configured to generate an ultrasonic image; a body housing configured to house the main body; a display/operation panel configured to operate the main body and display the ultrasonic image; and a lifter on which the display/operation panel is placed, the lifter being attached to the body housing and configured to adjust height of the display/operation panel from a floor in each of an electric mode (i.e., automatic mode) and a manual mode.

Hereinafter, embodiments of the present invention will be described by referring to the accompanying drawings.

(Overall Configuration)

Figure 1:
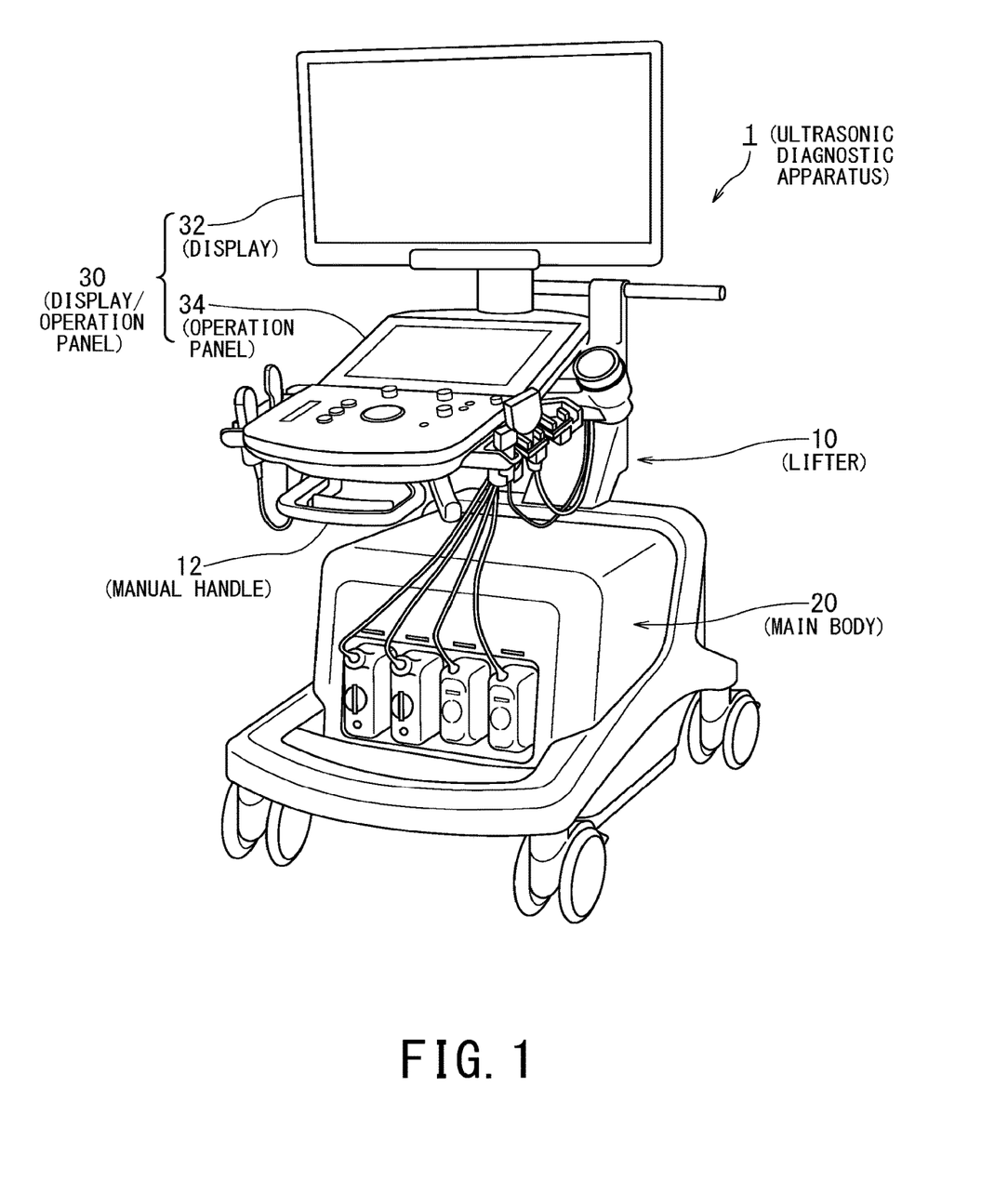
FIG. 1 is a perspective view illustrating an appearance of the ultrasonic diagnostic apparatus according to the present embodiment.
Figure 2A:
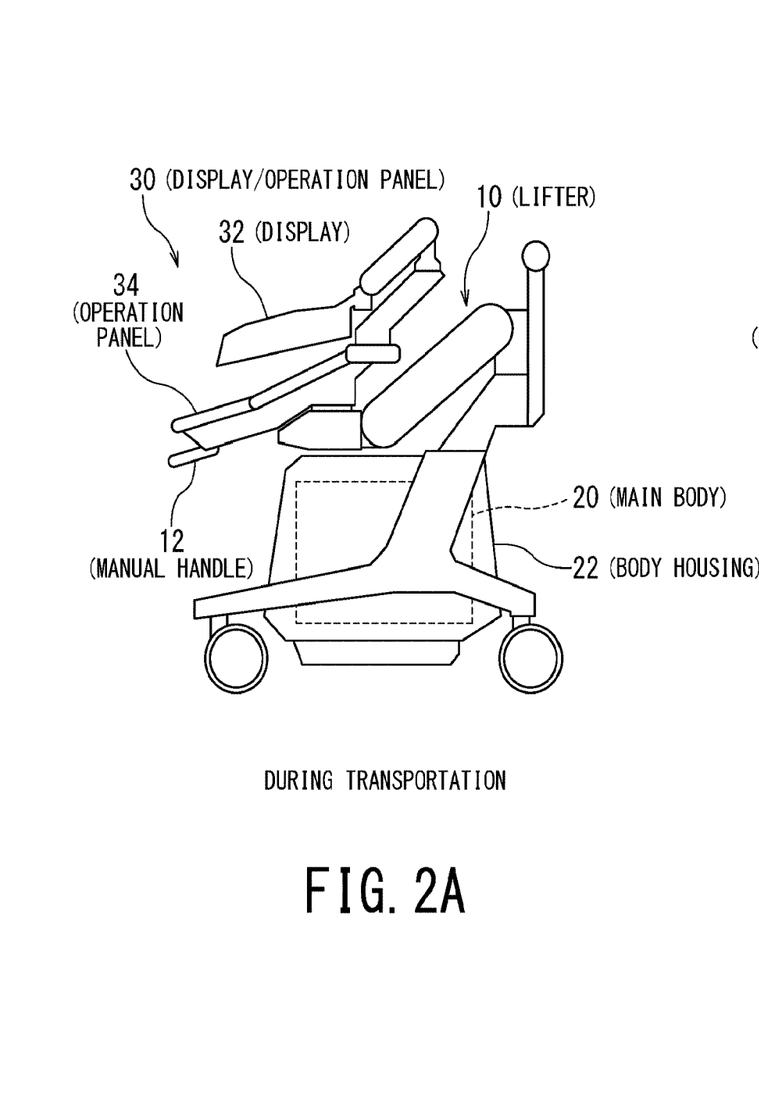
FIG. 2A and FIG. 2B are schematic side views illustrating the appearance of the ultrasonic diagnostic apparatus during operation and when being moved.
Figure 2B:
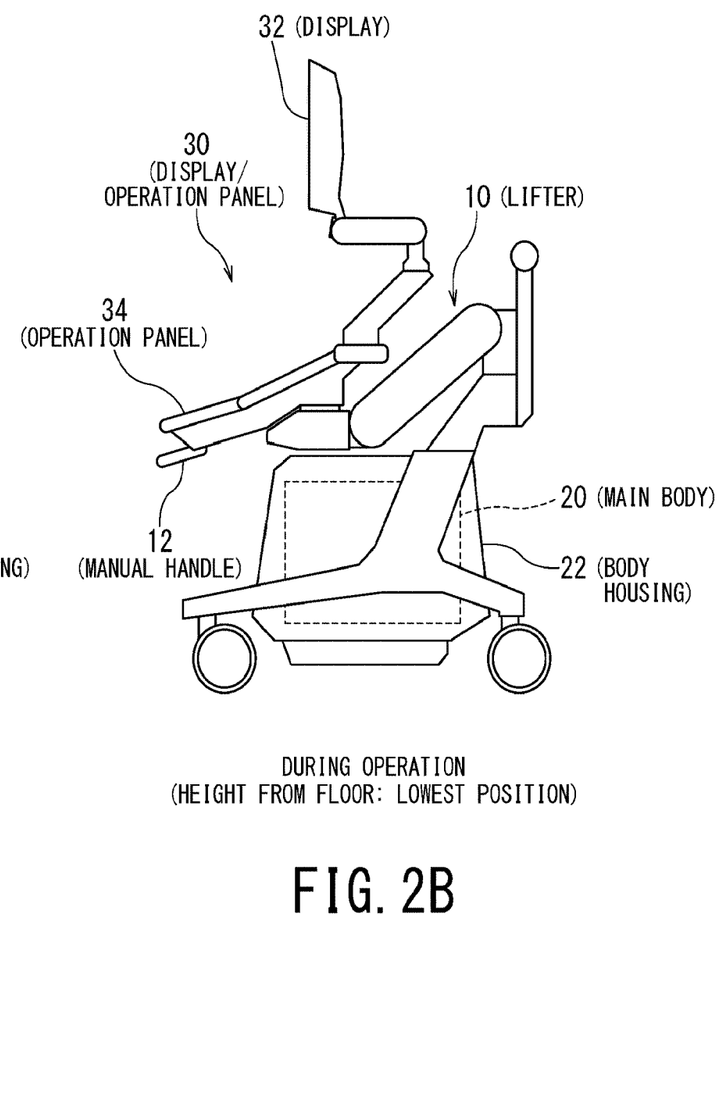

FIG. 1 is a perspective view illustrating the appearance of the ultrasonic diagnostic apparatus 1 according to the present embodiment. FIG. 2A is a schematic side view illustrating the appearance of the ultrasonic diagnostic apparatus 1 during transportation. FIG. 2B is a schematic side view illustrating the appearance of the ultrasonic diagnostic apparatus 1 during operation.

As shown in FIG. 1, FIG. 2A and FIG. 2B, the ultrasonic diagnostic apparatus 1 includes a main body 20, a lifter 10, and a display/operation panel 30.

The main body 20 may be a main component of the ultrasonic diagnostic apparatus 1 excluding the lifter 10, the display/operation panel 30, and an ultrasonic probe. The main body 20 generates ultrasonic image data from ultrasonic signals acquired by using the ultrasonic probe. The main body 20 causes the display 32 to display an ultrasonic image based on the generated ultrasonic image data and stores the data in the main body 20.

The main body 20 is housed in the body housing 22 as shown in FIG. 2A and FIG. 2B. The body housing 22 includes, for example, four casters. A user can move the ultrasonic diagnostic apparatus 1 while grasping a moving handle that is provided on the lifter 10.

The lifter 10 connects the display/operation panel 30 to the body housing 22 and supports the display/operation panel 30 such that the display/operation panel 30 can be lifted up and lowered down in both of the manual mode and the electric mode as described below.

The display/operation panel 30 includes a display 32 and an operation panel 34. As described above, the display 32 displays various ultrasonic images such as a B-mode image and a color Doppler image on the basis of the ultrasonic image data generated by the main body 20. The display 32 also displays various data and information related to the ultrasonic images and operation of this apparatus 1. The display 32 includes, for example, a liquid crystal panel or an organic EL (Electro Luminescence).

The operation panel 34 is a device for inputting data and settings of various operations of the ultrasonic diagnostic apparatus 1. The operation panel 34 includes, for example, a switch panel and a touch panel as illustrated in FIG. 1. A trackball, various switches, and dials are disposed on the switch panel. The touch panel is configured such that the user can input various data and information by touching the panel surface according to the displayed contents on the panel.

As shown in FIG. 2A, the display 32 is usually folded so as to be superimposed over the operation panel 34, while the ultrasonic diagnostic apparatus 1 being moved or transported from one inspection location to the next inspection location, or stored in the specified storage location in the non-operation state.

On the other hand, during the operation of the ultrasonic diagnostic apparatus 1, as shown in FIG. 2B, the display 32 is unfolded such that its display screen faces the user.

Note that the height of the display/operation panel 30 from the floor surface is adjustable. Though FIG. 2B shows the state of the display/operation panel 30, including the display 32 and the operation panel 34, at the lowest position from the floor surface, a user, such as a doctor or an ultrasonic examination technologist, can adjust the height of the display/operation panel 34 to a position where the medical image can be readily observed or the user can readily operate the ultrasonic diagnostic apparatus 1, depending on the posture of the user when examining the object and/or the height and sitting height of the user.

Figure 3A:
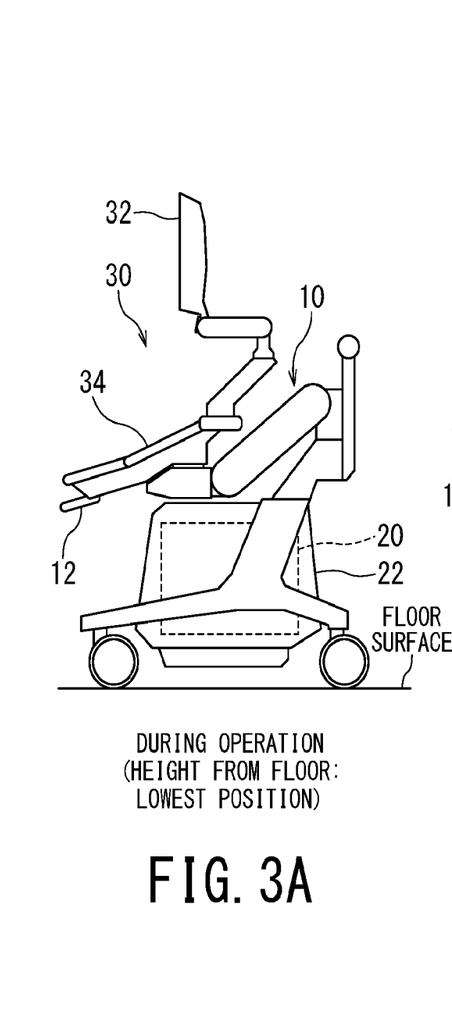
FIG. 3A to FIG. 3C are schematic side views illustrating height adjustment of a display/operation panel.
Figure 3B:
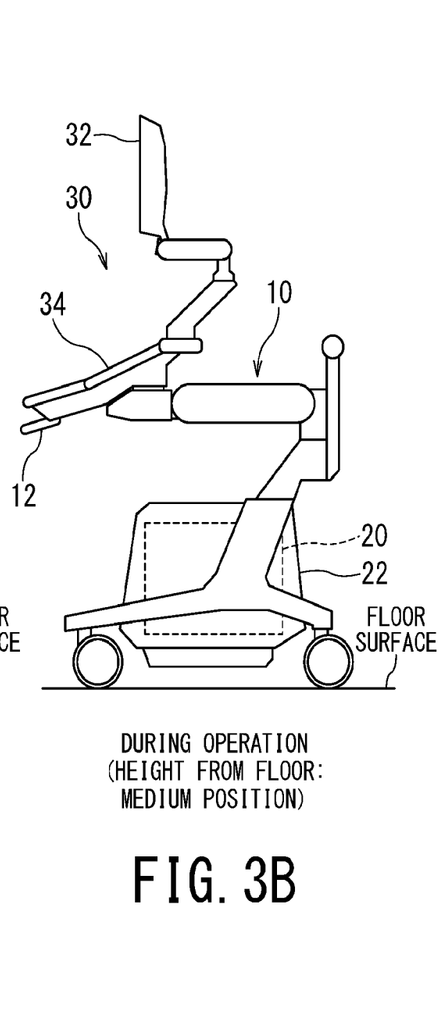
Figure 3C:
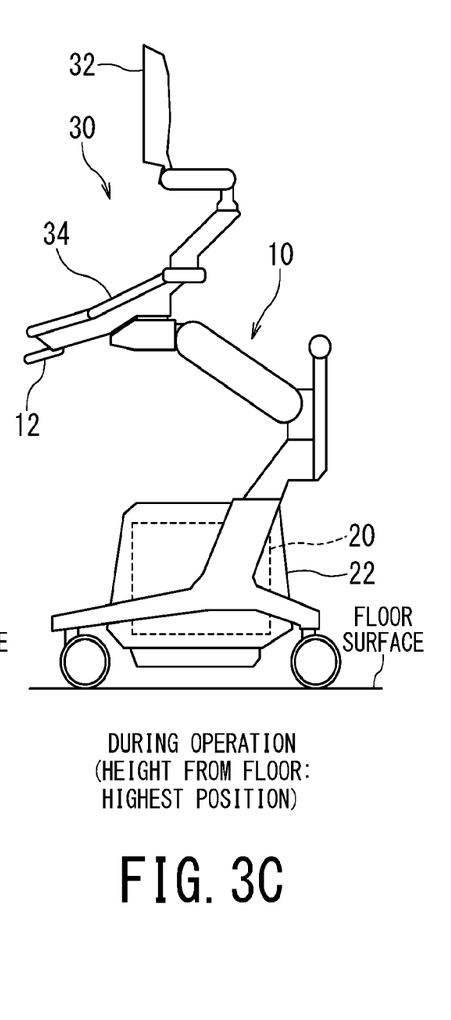

FIG. 3A to FIG. 3C are schematic side views illustrating the height adjustment of the display/operation panel 30 performed by the ultrasonic diagnostic apparatus 1 of the present embodiment.

FIG. 3A shows the state where the display/operation panel 30 is at the minimum height (i.e., lowest position) from the floor surface like FIG. 2B. In the state of this lowest position, a support arm 100 of the lifter 10 (See FIG. 4) is tilted downward by, for example, −40 degrees so as to bring the placing pedestal 102 (See also FIG. 4) provided at the tip of support arm 100 to the lowest position as described below. As a result, the display/operation panel 30 placed on the placing pedestal 102 is also brought to the lowest position.

FIG. 3B shows the state where the display/operation panel 30 is at the medium height (i.e., medium position) from the floor surface. In the state of this medium position, the support arm 100 of the lifter 10 is almost horizontal such that the placing pedestal 102 provided at the tip of the support arm 100 becomes higher than in the lowest position shown in FIG. 3A. As a result, the display/operation panel 30 placed on the placing pedestal 102 is also lifted to the medium height.

FIG. 3C shows the state where the display/operation panel 30 is the highest (i.e., highest position) from the floor surface. In the state of this highest position, the support arm 100 of the lifter 10 is tilted upward, by, for example, +40 degrees such that the placing pedestal 102 provided at the tip of the support arm 100 is brought to the highest position. As a result, the display/operation panel 30 placed on the placing pedestal 102 is also brought to the highest position.

(Lifter)

As described above, the height adjustment of the display/operation panel 30 in the ultrasonic diagnostic apparatus 1 of the present embodiment is mainly performed by the movement of the lifter 10. Hereinbelow, the configuration and operation of the lifter 10 will be described.

Figure 4:
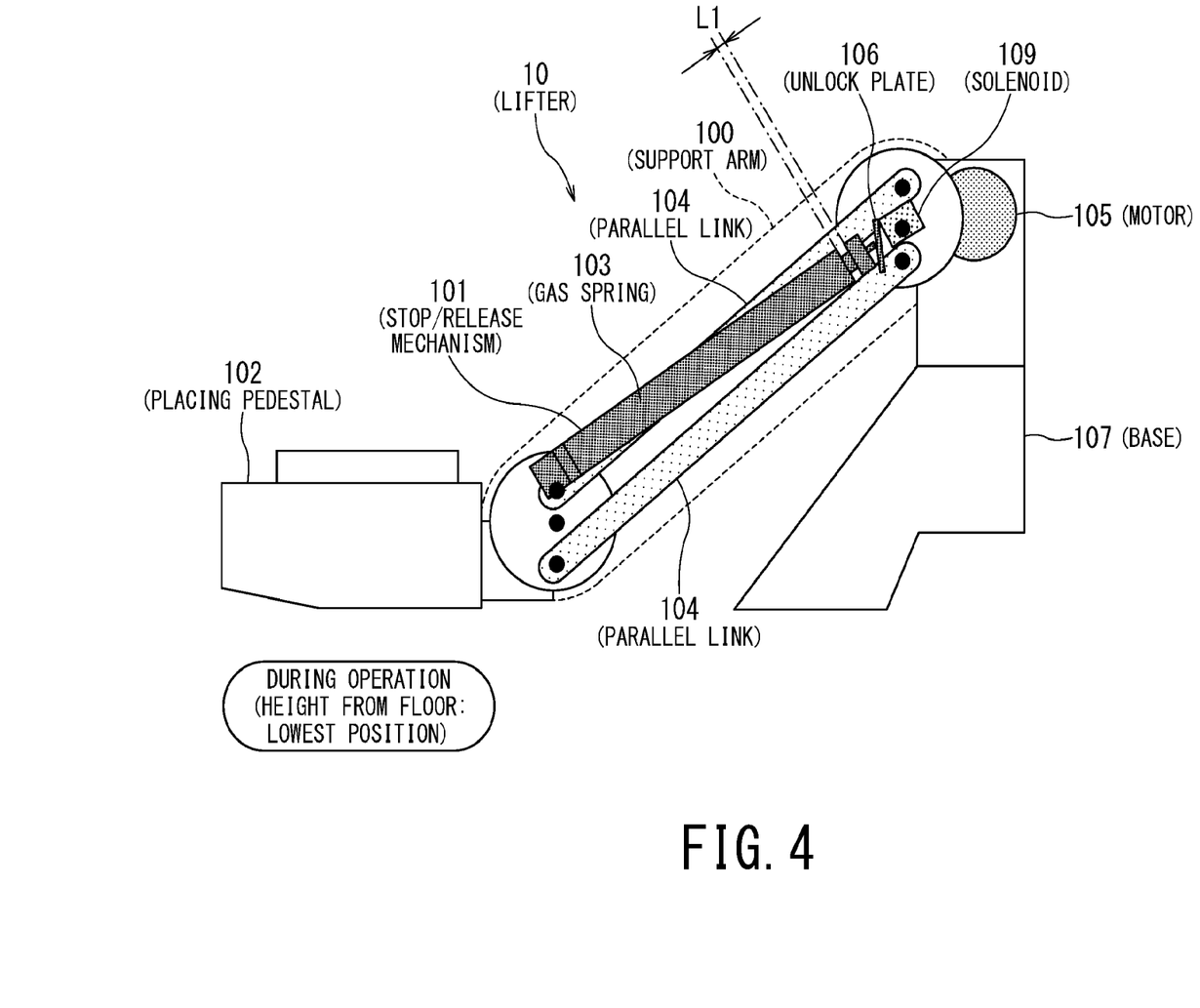
FIG. 4 is a first schematic diagram illustrating the internal structure of the lifter and an operation of a gas spring.

FIG. 4 is a side view of the lifter 10 and is a schematic diagram illustrating the internal structure of the lifter 10.

Figure 5:
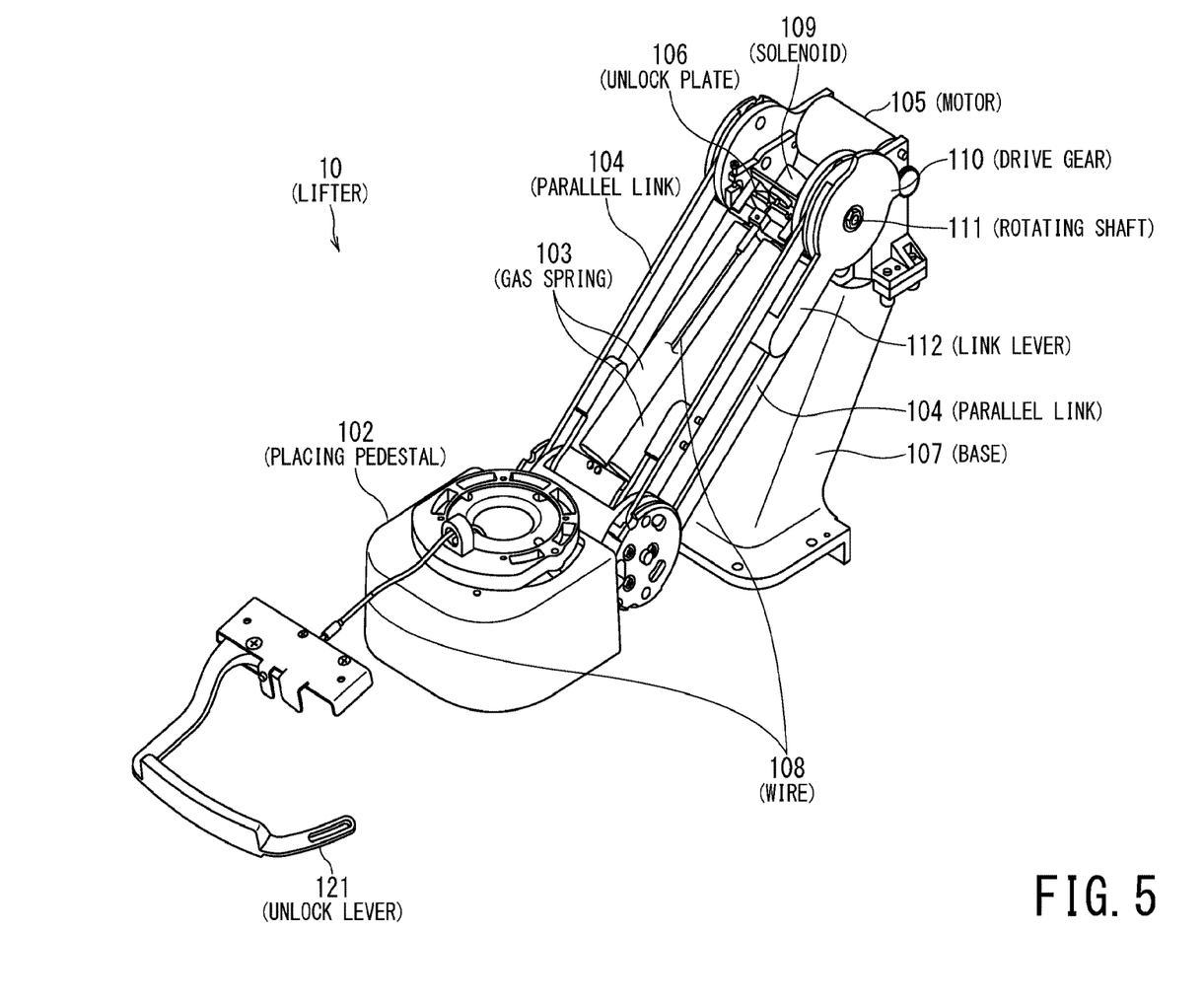
FIG. 5 is a second schematic diagram illustrating the internal structure of the lifter.

FIG. 5 is a perspective view illustrating the internal structure of the lifter 10, in particular, the internal structure of the support arm 100.

As shown in FIG. 4, the lifter 10 includes a base 107, the support arm 100, and the placing pedestal 102. The lower end of the base 107 is fixed to body housing 22 and the upper end of the base 107 is connected to the support arm 100 such that the base 107 tiltably supports one end of the support arm 100. Above the base 107, a motor 105 for electrically driving the support arm 100 is accommodated.

The placing pedestal 102 for placing the display/operation panel 30 is connected to the other end of the support arm 100 (i.e., connected to the end opposite to the connection portion with the base 107). Ahead of the placing pedestal 102, a manual handle 12 and an unlock lever 121 are provided. The manual handle 12 is fixed to the bottom face of the operation panel 34 of the display/operation panel 30, for example (FIG. 1).

In the manual mode, while holding the manual handle 12 and moving the unlock lever 121 to maintain the support arm 100 in the unlocked state, the user can lift (i.e., raise) and lower the display/operation panel 30 by moving the manual handle 12 up and down (i.e., in the vertical direction).

An annular turntable is provided at the top of the placing pedestal 102, as shown in FIG. 5. The user can rotate the display/operation panel 30 placed on the annular turntable on the placing pedestal 102 in the azimuth direction by moving the manual handle 12 in the right-left direction.

As shown in FIG. 4, the support arm 100 includes a pair of parallel links 104 and a stop/release mechanism (i.e., stop/release regulator) 101. The parallel links 104 are the main structural components of the support arm 100. The parallel links 104 rotate the support arm 100 in the elevation direction around the rotating shaft 111 (See FIG. 5), while supporting the weight of the display/operation panel 30 placed on the placing pedestal 102.

The stop/release mechanism 101 includes, for example, a pair of gas springs 103 and an unlocking member (such as an unlock plate 106), and regulates the movement of the support arm 100. More detailed operations of the gas springs 103 and the unlock plate 106 will be described below.

As shown in FIG. 5, the support arm 100 includes a pair of parallel links 104. One of the parallel links 104 is on the back side and the other of the parallel links 104 is on the front side as shown in FIG. 5. Two gas springs 103 are disposed so as to be sandwiched between the pair of parallel links 104.

The unlock plate 106 and a solenoid 109 are disposed near the end of the gas springs 103 on the side of the motor 105. One end of a wire 108 is fixed to the unlock plate 106. The wire 108 passes from the unlock plate 106 to the unlock lever 121 through the inside of the support arm 100 and the placing pedestal 102.

In the manual mode, when the user moves the unlock lever 121, the wire 108 is pulled towards the manual handle 12. In conjunction with this movement of the wire 108, the unlock plate 106 fixed to the end of the wire 108 is slightly tilted toward the side of the manual handle 12, and thereby, the gas springs 103 are unlocked. In the unlocked state, when the user moves the manual handle 12 up and down, the support arm 100 is rotated around the rotating shaft 111, and consequently, the user can manually move the display/operation panel 30 placed on the placing pedestal 102 up and down.

In the electric mode, the unlock plate 106 is tilted toward the manual handle 12, similar to the case of the manual mode, by the electromagnetic force of the solenoid 109. Accordingly, the gas springs 103 are unlocked. When the motor 105 is rotated in this unlocked state, the rotation of the motor 105 is propagated from a gear of the motor shaft to a drive gear 110. The drive gear 110 is configured such that one end thereof meshes with the gear of the motor shaft, and the other end thereof is inserted as a link lever 112 into the strip-shaped gap of the parallel links 104. With this configuration, when the motor 105 rotates, the link lever 112 rotates around the rotating shaft 111. In conjunction with this movement of the link lever 112, the parallel links 104 also rotate around the rotating shaft 111, which causes the support arm 100 to rotate around the rotating shaft 111, and consequently, the display/operation panel 30 placed on the placing pedestal 102 can be electrically moved up and down.

Figure 6:
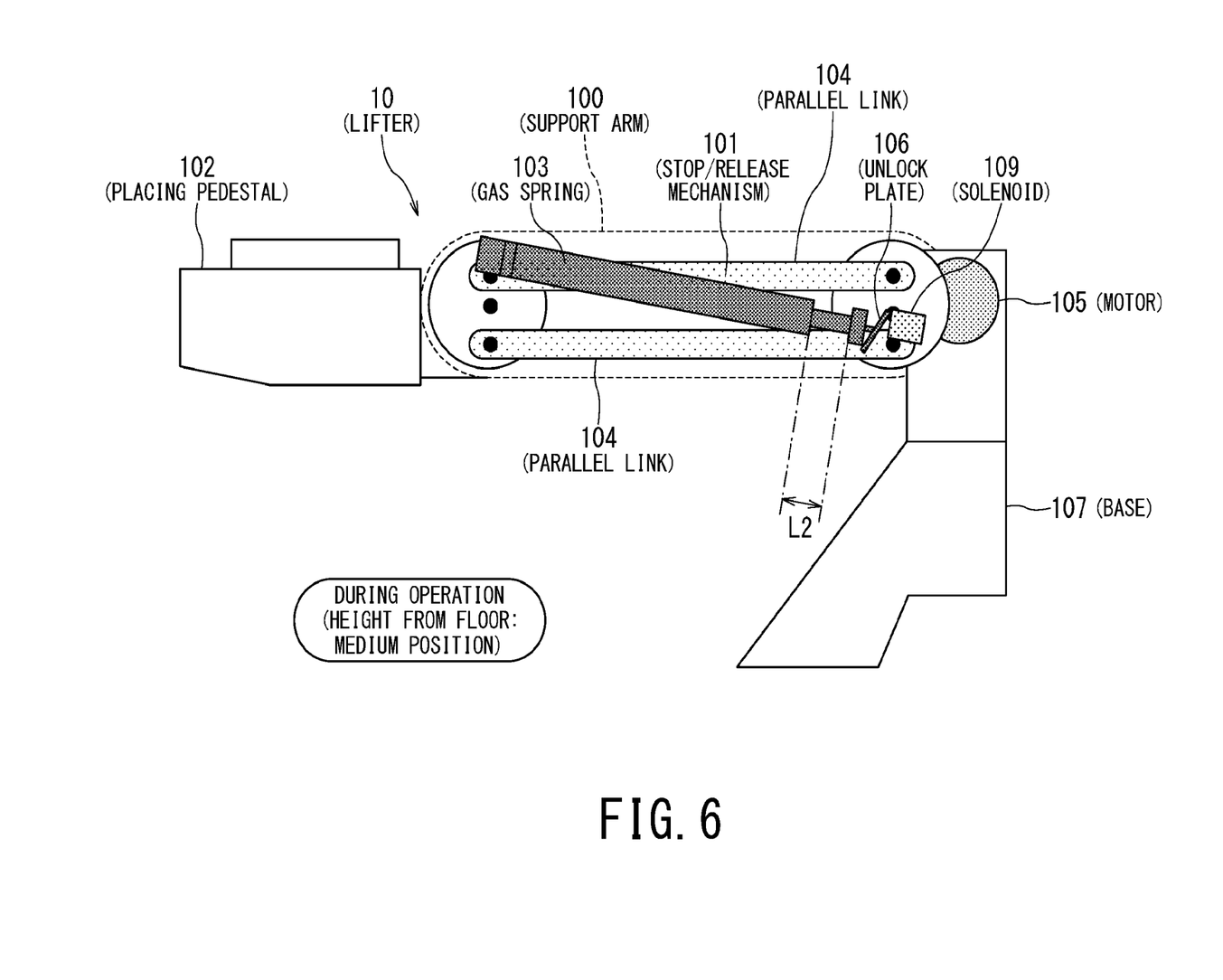
FIG. 6 is a second schematic diagram illustrating the operation of the gas spring of the present embodiment.
Figure 7:
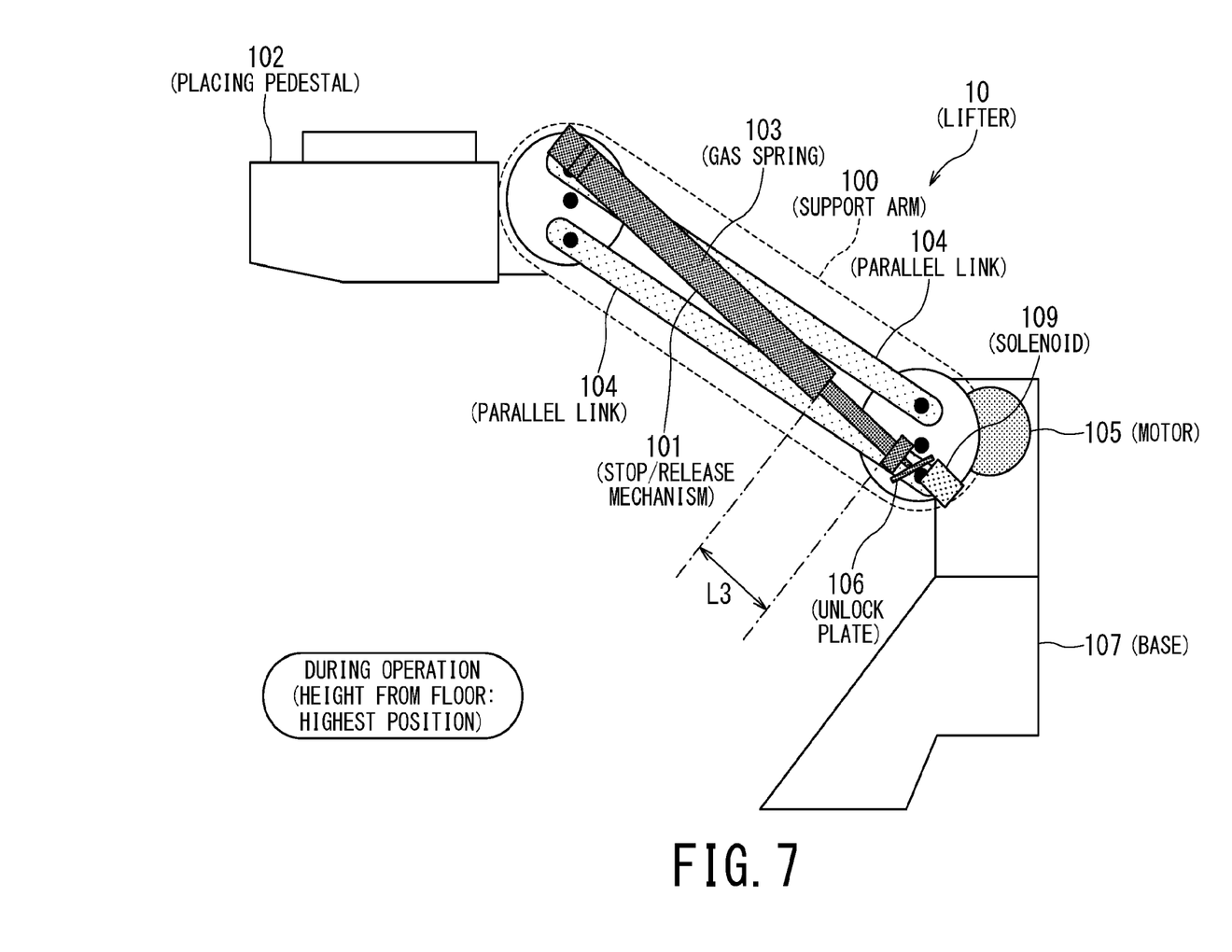
FIG. 7 is a third schematic diagram illustrating the operation of the gas spring of the present embodiment.

Next, the operation of the gas springs 103 used in the ultrasonic diagnostic apparatus 1 of the present embodiment will be described by referring to FIG. 4, FIG. 6, and FIG. 7. As shown in FIG. 4, FIG. 6, and FIG. 7, The gas spring 103 includes a cylinder, a disk-shaped piston inserted into the cylinder, and a piston rod connected to the piston. The gas spring 103 is attached to the support arm 100 such that its length changes depending on rotation amount of the support arm 100. As shown in FIG. 4, FIG. 6, and FIG. 7, a part of the piston rod protrudes from the cylinder. In accordance with the change in length of the support arm 100 depending on the rotation amount of the support arm 100, the length of the protruding portion of the piston rod also changes as L1 (FIG. 4), L2 (FIG. 6), and L3 (FIG. 7), wherein L1<L2<L3.

The inside of the gas spring 103 is filled with gas and oil, and the oil-filled region is separated by a piston with an orifice (i.e., hole through which oil passes). When the orifice is closed, the oil flow between the regions separated by the piston is stopped and the movement of the piston is stopped. In other words, the gas spring 103 is locked and the length of the gas spring 103 is fixed by closing the orifice. As a result, in both of the manual mode and the electric mode, the support arm 100 is fixed without rotation and the display/operation panel 30 is prohibited from moving up and down.

When the orifice is opened, the oil in the region separated by the piston can pass through the orifice and the piston can move. In other words, the gas springs 103 is unlocked and the length of the gas spring 103 becomes variable by opening the orifice. As a result, in both of the manual mode and the electric mode, the support arm 100 can be rotated and the display/operation panel 30 can be lifted up and lowered down.

Another role of gas springs 103 is to assist the force in lifting up the display/operation panel 30. The assisting force is caused by the reaction force of the gas compressed by the piston. As shown in FIG. 4, when the lifter 10 is at the lowest position, the piston is pushed deepest into the cylinder (i.e., length of the gas spring 103 is the shortest), and the reaction force of the gas is maximized. Thus, after unlocking, the force that assists in lifting the display/operation panel 30 becomes the largest. As the lifter 10 shifts to the medium position (FIG. 6) and further to the highest position (FIG. 7), the length of the gas spring 103 becomes longer and the reaction force of the compressed gas in the cylinder becomes smaller. Even in this situation, the reaction force of the gas acts in the direction of increasing the length of the gas spring 103 (i.e., in the direction of raising the position of the placing pedestal 102). Thus, in the manual mode, the load on the user at the time of lifting the display/operation panel 30 is reduced. Further, in the electric mode, the load on the motor 105 when lifting the display/operation panel 30 is reduced.

Figure 8:
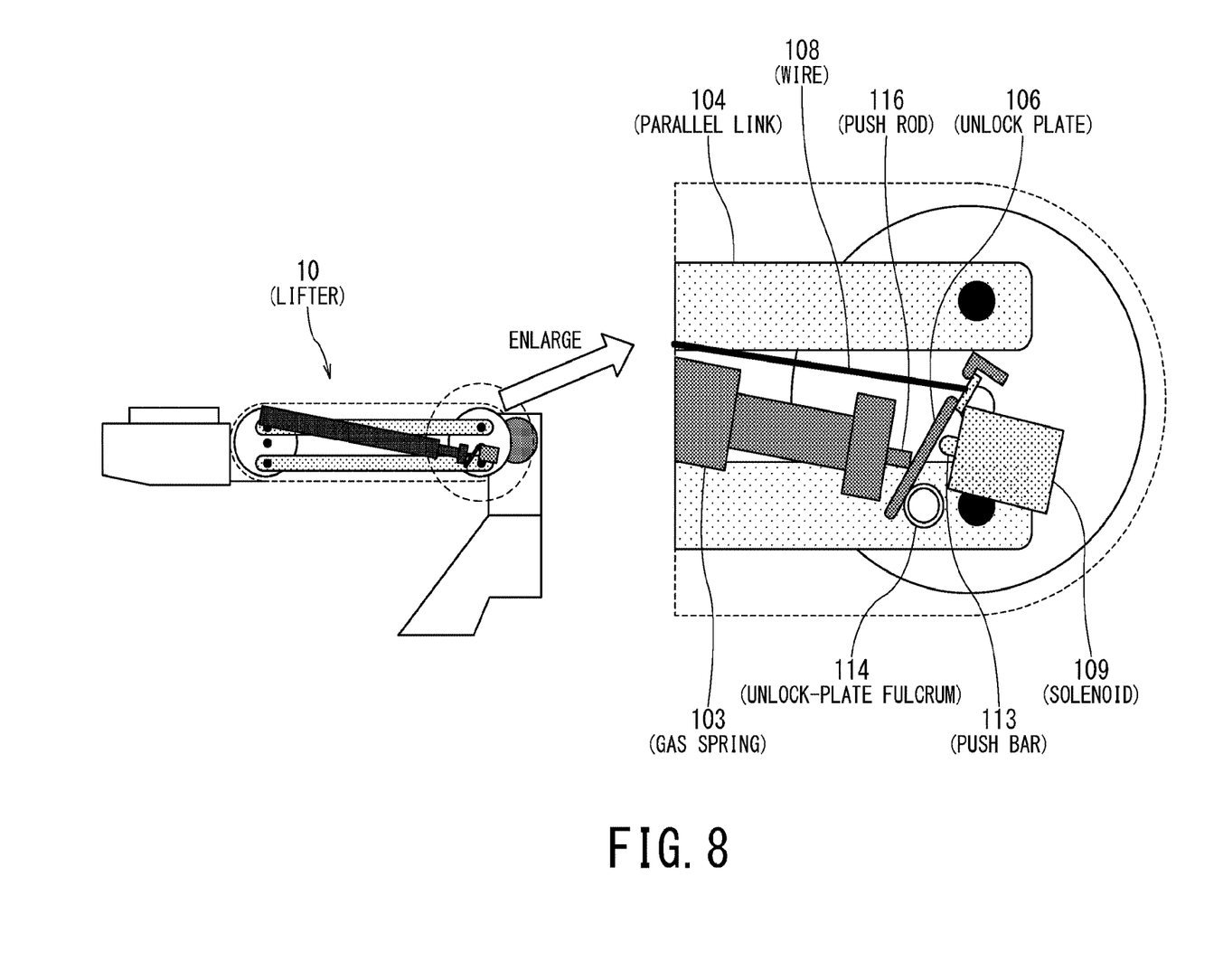
FIG. 8 is an enlarged view illustrating a detailed configuration in the vicinity of a base of a support arm.

Next, the locking/unlocking mechanism of the lifter 10 will be described by referring to FIG. 8 to FIG. 10B. FIG. 8 is an enlarged view of the detailed configuration of the support arm 100 near the base 107.

As shown in the right part of FIG. 8, at the end of each gas spring 103 on the side of the base 107, a push rod 116 protrudes. The push rod 116 is connected to a valve that opens and closes the orifice. In addition, an unlock plate 106 is placed so as to contact the push rod 116. The unlock plate 106 is an unlocking member for pushing the push rod 116 into the inside of the gas spring 103. Although the unlocking member does not necessarily have to be a plate-shaped member, in the following description, it is assumed that the unlocking member is an unlock plate 106.

One end of the unlock plate 106 is supported by the unlock-plate fulcrum 114 and is configured to be able to rotate around a contact point with the unlock-plate fulcrum 114. The end of the wire 108 is fixed to the other end of the unlock plate 106.

The face of the unlock plate 106 opposite to the face that contacts the push rod 116 is in contact with the push bar 113 that is part of the solenoid 109. The push bar 113 is configured to be able to expand and contract by the electromagnetic force of the solenoid 109.

Figure 9A:
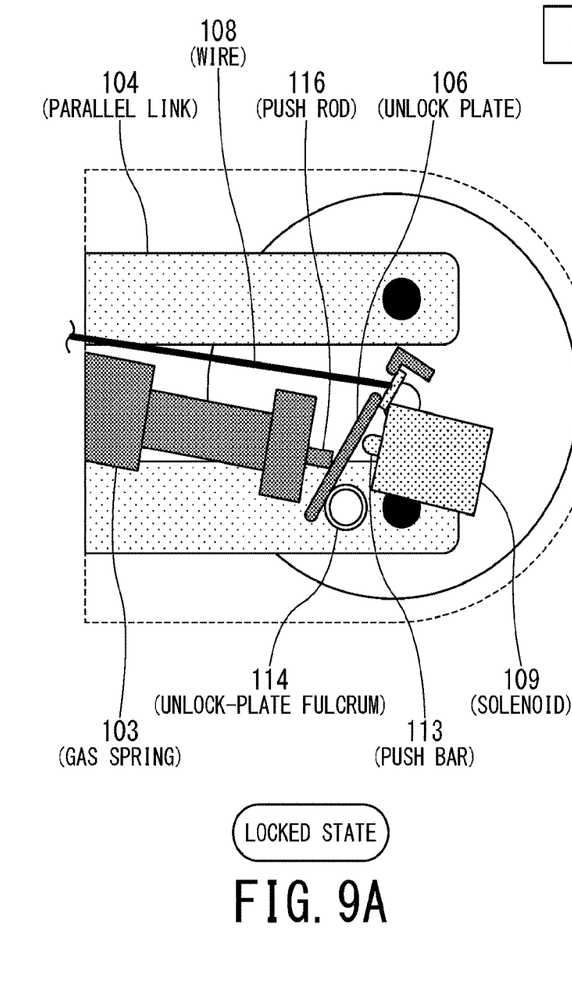
FIG. 9A and FIG. 9B are schematic diagrams illustrating a manual unlocking mechanism.
Figure 9B:
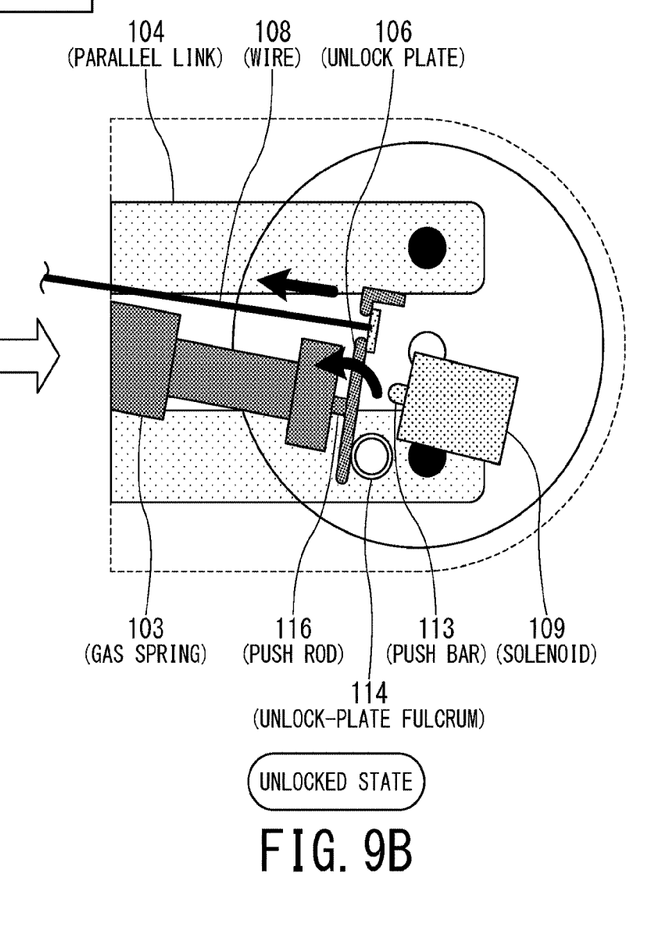

FIG. 9A and FIG. 9B are schematic diagrams illustrating the manual unlocking mechanism. FIG. 9A is a schematic diagram illustrating a locked state and is the same as the right figure of FIG. 8. The locked state is a state in which the push rod 116 of the gas spring 103 protrudes from the inside of the gas spring 103. In this state, the gas spring 103 is configured such that the valve of the orifice inside the gas spring 103 is closed. As a result, the length of the gas spring 103 is fixed, and the rotation of the support arm 100 is also fixed, i.e., locked.

FIG. 9B illustrates the unlocking operation in the manual mode. As described above, the wire 108 passes from the unlock plate 106 to the unlock lever 121 through the inside of the support arm 100 and the placing pedestal 102. When the user moves the unlock lever 121, the wire 108 is pulled toward the manual handle 12. In conjunction with this movement, the unlock plate 106 fixed to the end of the wire 108 rotates counterclockwise in FIG. 9B around the contact point with the unlock-plate fulcrum 114. As a result, the push rod 116 in contact with the unlock plate 106 is pushed into the inside of the gas spring 103, resulting in that the gas spring 103 is brought into the unlocked state.

Figure 10A:
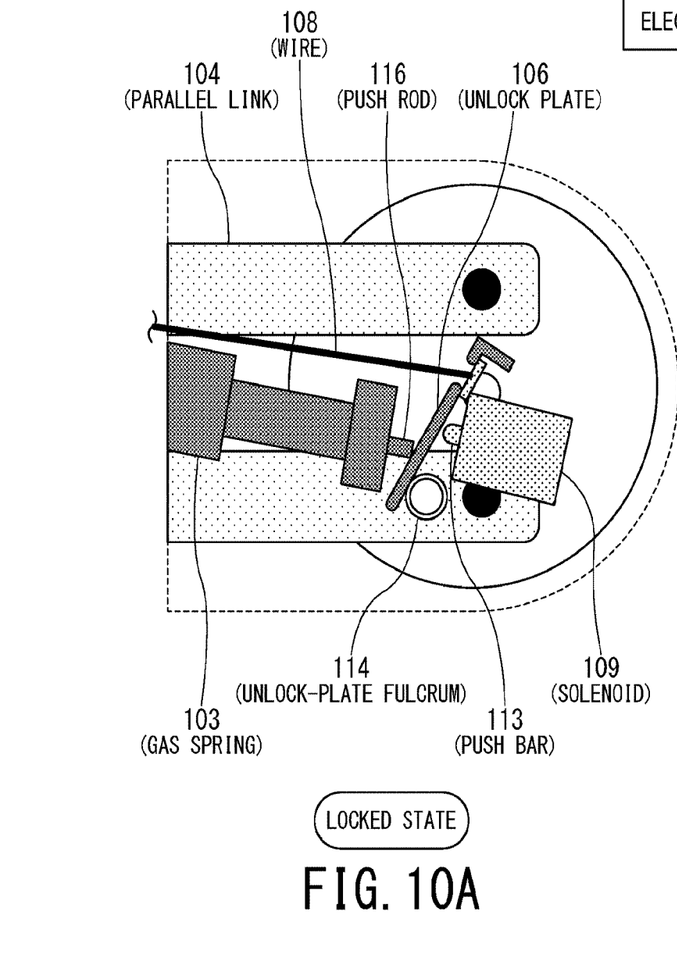
FIG. 10A and FIG. 10B are schematic diagrams illustrating an electric unlocking mechanism.
Figure 10B:
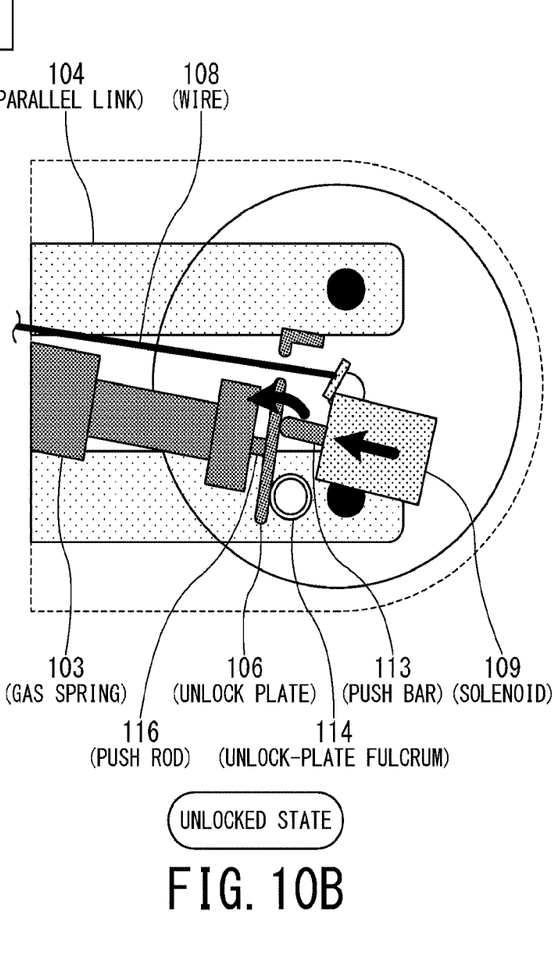

FIG. 10A and FIG. 10B are schematic diagrams illustrating the electric unlocking mechanism. FIG. 10A illustrates the locked state and is the same as the right figure of FIG. 8. FIG. 10B illustrates the unlocking operation in the electric mode. In the electric mode, an electric signal that activates the solenoid 109 (hereinafter, referred to as a solenoid-ON signal) is applied to the solenoid 109. In response to the application of the solenoid-ON signal, the push bar 113 of the solenoid 109 is pushed out from a main body of the solenoid 109. This extrusion of the push bar 113 causes the unlock plate 106 to rotate counterclockwise around the contact point with the unlock-plate fulcrum 114. As a result, the push rod 116 in contact with the unlock plate 106 is pushed into the inside of the gas spring 103 and the gas spring 103 is brought into the unlocked state, similar to the case of the manual mode. In the electric mode, after bringing the gas spring 103 into the unlocked state in the above-described manner, the motor 105 is activated to rotate the support arm 100 around the rotating shaft 111 in the forward or reverse direction such that the display/operation panel 30 is moved up and down.

When the solenoid-ON signal is turned off, the push bar 113 is pulled into the main body of the solenoid 109. As a result, the push rod 116 in contact with the unlock plate 106 is pushed out from the inside of the gas spring 103, and it returns to the locked state shown in FIG. 10A.

Figure 11:
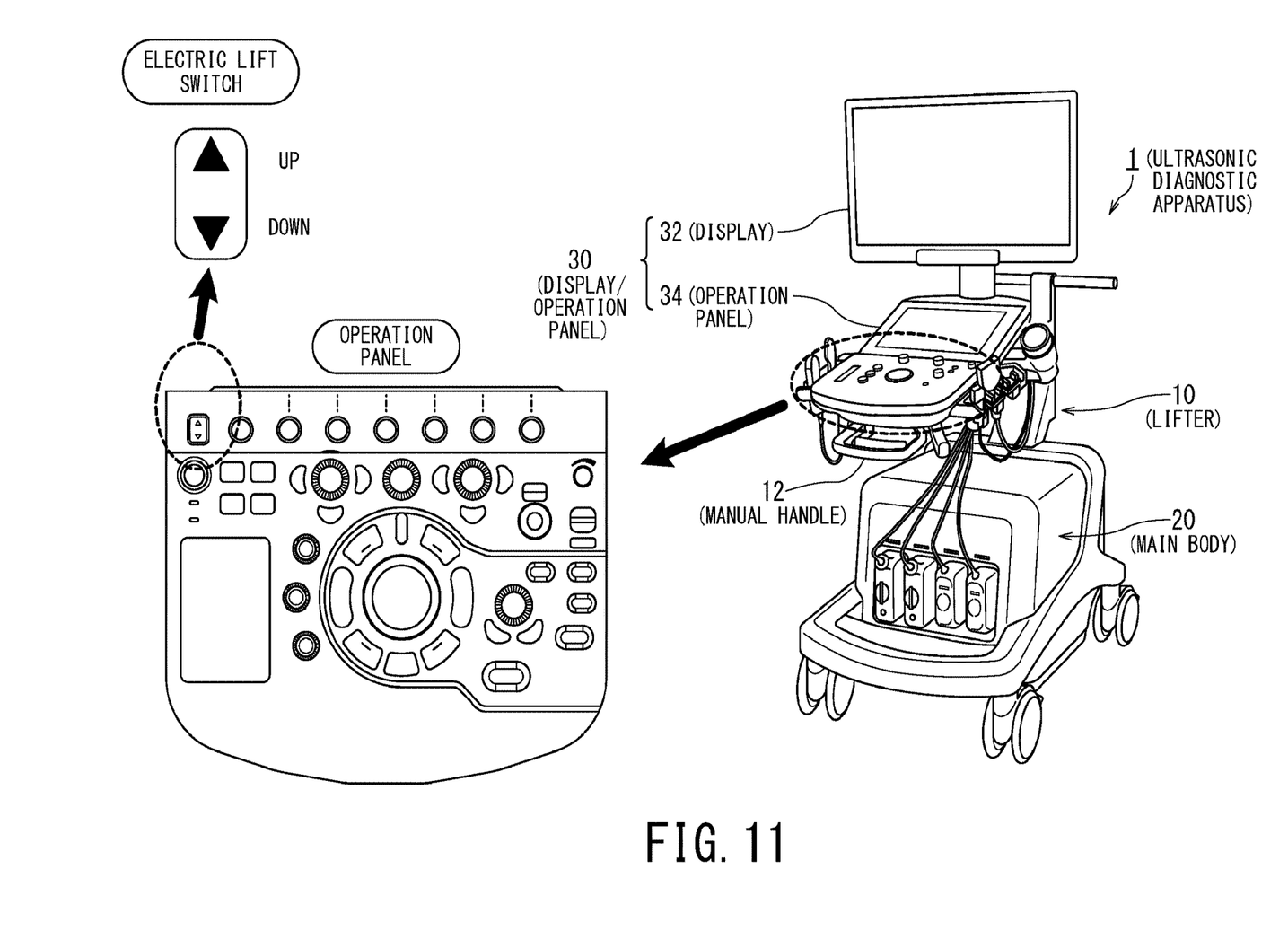
FIG. 11 is a schematic diagram illustrating the operation of lifting/lowering the display/operation panel in the electric mode.

FIG. 11 is a schematic diagram illustrating the operation of lifting/lowering the display/operation panel 30 in the electric mode. An electric lift switch (i.e., a switch for operating the lifting/lowering of the display/operation panel 30 in the electric mode) is provided, for example, in a part of the operation panel 34. The electric lift switch is configured as, for example, a three-position seesaw switch that includes an "UP" position, a neutral position, and a "DOWN" position. When the user switches the electric lift switch from its neutral position to the "UP" position, the solenoid-ON signal is applied to the solenoid 109 to release the lock state and the rotation of the motor 105 lifts up the display/operation panel 30. After that, when the user switches the electric lift switch back to the neutral position, the rotation of the motor 105 is stopped and the solenoid-ON signal is turned off, which returns the gas spring 103 to the lock state, and consequently, the movement of the support arm 100 is fixed.

When the user switches the electric lift switch from its neutral position to the "DOWN" position, the solenoid-ON signal is applied again to the solenoid 109 to release the lock state, and the motor 105 rotates in the reverse direction to lower the position of the display/operation panel 30. After that, when the user switches the electric lift switch back to the neutral position again, the rotation of the motor 105 is stopped and the solenoid-ON signal is turned off, which returns the gas spring 103 to the lock state, and consequently, the movement of the support arm 100 is fixed again.

When the electric lift switch is switched to either the "UP" position or the "DOWN" position, the operation mode is set to the electric mode and the display/operation panel 30 can be electrically lifted or lowered by the rotation of the motor 105.

The manual mode corresponds to the operation mode when the electric lift switch is switched to the neutral position, i.e., corresponds to the operation mode excluding the cases of lifting and lowering the display/operation panel 30 in the electric mode. When the electric lift switch is switched to the neutral position, i.e., in the manual mode, the user can manually lift or lower the display/operation panel 30 by operating the manual handle 12 and the unlock lever 121.

(Overall Functional Block)

Figure 12:
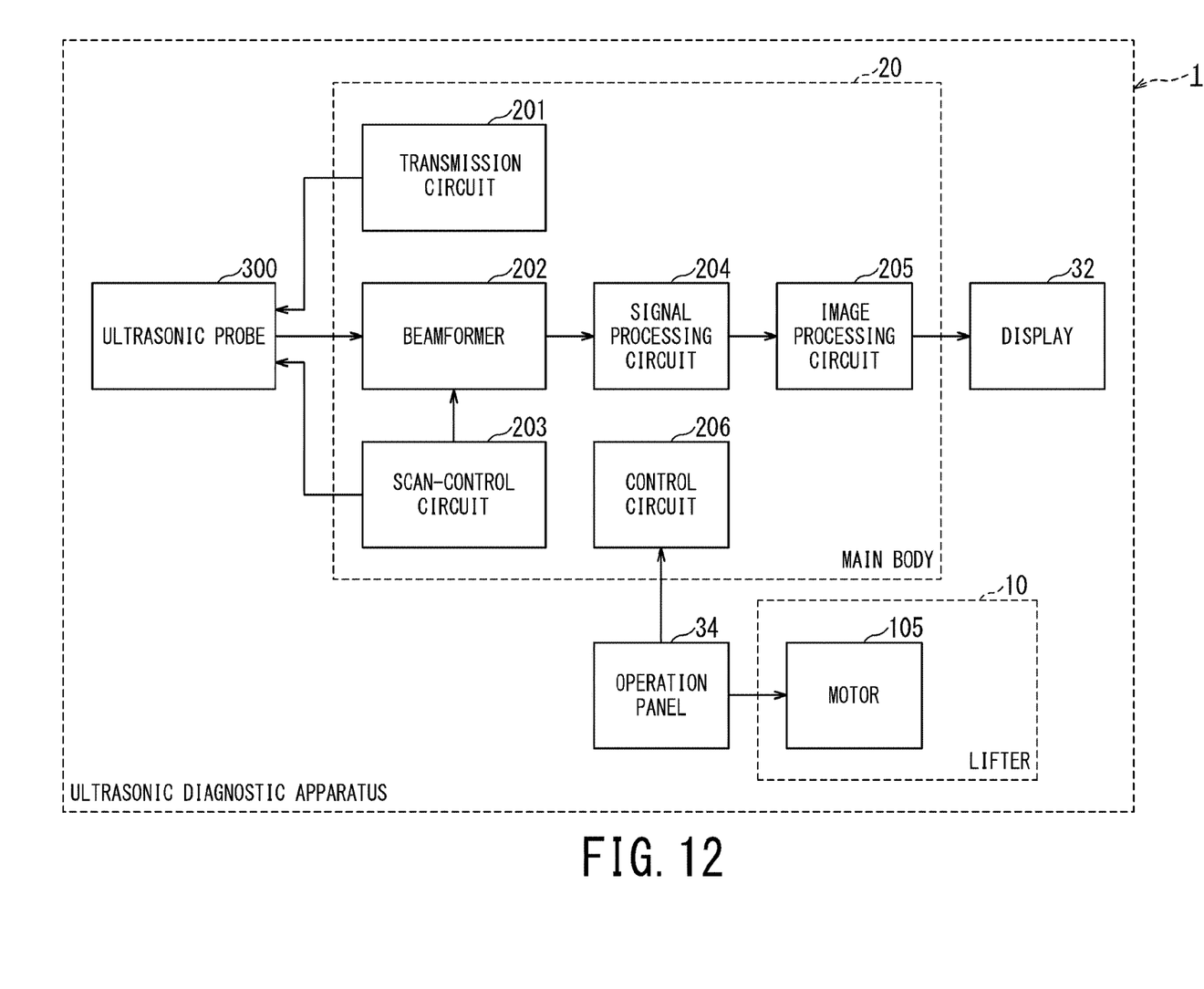
FIG. 12 is a block diagram illustrating a functional configuration of the ultrasonic diagnostic apparatus of the present embodiment.

FIG. 12 is a block diagram illustrating the functional configuration of the ultrasonic diagnostic apparatus 1 of the present embodiment. The ultrasonic diagnostic apparatus 1 includes, for example, an ultrasonic probe 300, the lifter 10, the main body 20, the display 32, and the operation panel 34. The main body 20 includes, for example, a transmission circuit 201, a beamformer 202, a scan-control circuit 203, a signal processing circuit 204, an image processing circuit 205, and a control circuit 206.

The ultrasonic probe 300 transmits an ultrasonic pulse generated by the transmission circuit 201 toward an object and receives the reflected wave from the object. The beamformer 202 forms a reception beam by performing processing including at least weighting addition on the reflected wave received by the ultrasonic probe 300. Further, the beamformer 202 scans the direction of the reception beam by the control signal from the scan-control circuit 203. The signal processing circuit 204 performs signal processing such as logarithmic detection processing, correlation processing, and Doppler processing on the received signal having been subjected to beam forming processing. The image processing circuit 205 generates images such as a B-mode image, a Doppler mode image, and a color Doppler mode image on, based on the signals after the signal processing and a scanning angle. The display 32 displays the generated images. The operation panel 34 includes a touch panel and an operation panel that has various switches such as a trackball and an electric lift switch. The control circuit 206 generates a control signal for controlling the respective components of the main body 20 on the basis of the operation information and data inputted from the operation panel 34. In addition, the signal based on the electric lift switch of the operation panel 34 is transmitted to the solenoid 109 and the motor 105 of the lifter 10, and is used for controlling the electric mode of the lifter 10.

According to the ultrasonic diagnostic apparatus 1 of each embodiment as described above, the lifter for adjusting the height of the display/operation panel of the ultrasonic diagnostic apparatus can be readily operated in both of the electric mode in which the panel is electrically lifted and lowered and the manual mode in which the panel is manually lifted and lowered.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus, comprising:
a main body configured to generate an ultrasonic image;
a body housing configured to house the main body;
a display/operation panel configured to operate the main body and display the generated ultrasonic image; and
a lifter configured to adjust a height of the display/operation panel from a floor in each of an electric mode and a manual mode; and
a motor configured to move the lifter up and down,
wherein; in the electric mode, the lifter is moved up and down with the motor in an on state, while in the manual mode, the lifter is moved up and downwith the motor in an off state.

2. The ultrasonic diagnostic apparatus according to claim 1, wherein the manual mode is an operation mode of the lifter except when the lifter lifts or lowers the display/operation panel in the electric mode.

3. The ultrasonic diagnostic apparatus according to claim 1, wherein the lifter comprises:
a placing pedestal on which the display/operation panel is placed;
a support arm configured to support the placing pedestal;
the motor, which configured to adjust a height of the placing pedestal in the electric mode by electrically moving the support arm;
a handle configured to adjust the height of the placing pedestal in the manual mode when the support arm is manually moved; and
a stop/release mechanism that is connected to the support arm and prohibits and releases movement of the support arm in each of the electric mode and the manual mode.

4. The ultrasonic diagnostic apparatus according to claim 3, wherein the stop/release mechanism comprises:
a gas spring configured to be variable in length, lock a movement thereof in a length direction when a movement of the support arm is prohibited, and unlock the movement in the length direction thereof when a prohibition of the movement of the support arm is released, wherein the gas spring includes a push rod configured to protrude and retract from one end of the gas spring so as to switch between locking and unlocking; and
an unlocking member configured to perform the unlocking by pushing the push rod into the gas spring.

5. The ultrasonic diagnostic apparatus according to claim 4, wherein:
the lifter includes a base configured to be attached to the body housing;
one end of the support arm is connected to the placing pedestal;
another end of the support arm is pivotally supported by a rotation shaft provided on a base; and
the height of the display/operation panel from the floor is adjusted by causing the support arm to rotate around the rotating shaft.

6. The ultrasonic diagnostic apparatus according to claim 5, wherein the gas spring is connected to the support arm in such a manner that a length of the gas spring changes depending on a rotation amount of the support arm.

7. The ultrasonic diagnostic apparatus according to claim 4, wherein:
the lifter further comprises a solenoid configured to move the unlocking member in a direction of pushing the push rod into the gas spring; and
the lifter is configured to adjust the height of the display/operation panel from the floor in the electric mode by using an electromagnetic force of the solenoid to move the unlocking member to unlock the gas spring, and then by using a rotation of the motor to rotate the support arm in a forward or reverse direction.

8. The ultrasonic diagnostic apparatus according to claim 4, wherein:
the lifter further comprises a wire stretched between the handle and the unlocking member; and
the lifter is configured to adjust the height of the display/operation panel from the floor in the manual mode by pulling the wire in accordance with a manual operation on the handle to unlock the gas spring, and then by moving the handle in accordance with the manual operation on the handle.

9. The ultrasonic diagnostic apparatus according to claim 1, wherein the lifter is configured to carry the display/operation panel thereon and is attached to the body housing.

* * * * *